(12) United States Patent
Comely et al.

(10) Patent No.: US 6,821,783 B1
(45) Date of Patent: Nov. 23, 2004

(54) TRANSITION METAL COMPLEXES AS LINKERS

(75) Inventors: Alex C Comely, London (GB); Sue E Gibson, London (GB); Neil J Hales, Macclesfield (GB); Mark A Peplow, Hamilton (CA)

(73) Assignee: Astrazeneca AB, Sweden (SE)

( * ) Notice: Subject to any disclaimer, the term of this patent is extended or adjusted under 35 U.S.C. 154(b) by 0 days.

(21) Appl. No.: 09/744,908

(22) PCT Filed: Jul. 29, 1999

(86) PCT No.: PCT/GB99/02499

§ 371 (c)(1),
(2), (4) Date: Jan. 31, 2001

(87) PCT Pub. No.: WO00/07966

PCT Pub. Date: Feb. 17, 2000

(30) Foreign Application Priority Data

Jul. 31, 1998 (GB) .............................................. 9816575

(51) Int. Cl.⁷ .............................................. G01N 37/00
(52) U.S. Cl. .............................. 436/56; 556/11; 556/20
(58) Field of Search .............................. 436/56; 656/11, 656/20

(56) References Cited

U.S. PATENT DOCUMENTS 6,057,465 A * 5/2000 Gallop .......................... 556/11

OTHER PUBLICATIONS

M.J. Plunkett: "Germanium and silicon linking strategies for traceless solid–phase synthesis" Journal of Organic Chemistry, vol. 62, No. 9, May 2, 1997, pp. 2885–2893, XP002121797 Easton US, pp. 2885–2888.

I. Sucholeiki: "Solid–phase photochemical C–S bond cleavage of thioethers—a new approach to the sold–phase production of non–peptide melecules" Tetrahedron Letters, vol. 35, No. 40, 1994, pp. 7307–7310, XP002121798 Oxford GB, cited in the application, the whole document.

B. Chenera: "Photo detachable arylsilane polymer linkages for use in solid phase organic synthesis" Journal of the American Chemical Society, vol. 117, No. 48, 1995, pp. 11999–12000, XP002121799 DC US, cited in the application, the whole document.

M.F. Semmelhack: "SNAR reactions with fluoroarene–Cr 9C0) 2L complexes, where L is a potential linker ligand for solid phase synthesis" Tetrahedron Letters, , vol. 39, No. 42, Oct. 15, 1998, pp. 7683–7686, XP002121800 Oxford GB figure 1.

S.E. Gibson: "Chromium carbonyl complexes as novel traceless linkers" Tetrahedron Letters, vol. 40, No. 7, Feb. 12, 1999, pp. 1417–1418, XP002121801 Oxford GB the whole document.

* cited by examiner

*Primary Examiner*—Jill Warden
*Assistant Examiner*—Monique T. Cole
(74) *Attorney, Agent, or Firm*—Fish & Richardson P.C.

(57) ABSTRACT

The invention relates to new traceless linkers which use transition metal complexes to link a π-orbital containing substrate for subsequent synthesis by, for example, combinatorial chemistry or multiple parallel synthesis (MPS) to a support.

8 Claims, 4 Drawing Sheets

Where hv is ultraviolet light
rt is room temperature
py is pyridine

Fig.1.

Where hv is ultraviolet light
rt is room temperature
py is pyridine

Scheme 1

Fig.3.(Cont.)

Scheme 2 scheme 3

TRANSITION METAL COMPLEXES AS LINKERS

The invention relates to new traceless linkers which use transition metal complexes to link a π-orbital containing substrate for subsequent synthesis by, for example, combinatorial chemistry or multiple parallel synthesis (MPS) to a support.

Combinatorial chemistry and MPS are techniques that are of great value in the efficient production of large numbers of molecules. Such large collections of molecules are of use in screening for useful properties or effects. The development of combinatorial chemistry and of MPS has been greatly facilitated by the use of solid-phase-synthesis in which substrate molecules are covalently attached to a solid support. The product of the reaction can be isolated by mechanically separating the solid support from the other components of the reactions and the product separated from the solid support by, for example, chemical cleavage. The whole process can be carried out quickly and efficiently and in many cases can be automated.

Members of a set of molecules made by combinatorial chemistry or MPS will have a recognisable common framework inherited from each different substrate and optionally modified during the combinatorial chemical steps. Disposed about the framework are the variable parts that derive from combinatorial modification of the substrate, for instance by combinatorial refunctionalisation of its functional groups. It is the variation in these parts that determines the diversity of the collection of molecules.

In most examples of solid-phase-synthesis the substrate is attached to the solid support through a covalent bond formed by functional groups on the substrate and support, for example by the formation of a carboxamide group between the support and the substrate.

This has three main limitations:
1. The functional group that is used to bind the substrate could have been used to introduce further variable reagents. This lost opportunity is a combinatorial reduction in the potential diversity of the molecules produced.
2. Although the object is to produce sets of compounds of great diversity in order to screen for useful properties or effects, the functional group that is linked to the support is a feature that all members of the combinatorial set of compounds share so that the diversity of the compounds produced is compromised by this common feature.
3. The chemistry required to attach a molecule through a functional group to a support varies as the functional group varies. In general, each different functional group will need to be linked to a support that has been specially prepared to react with it. Each differently linked functional group will need a different chemical treatment to release it from the support. Each different linking functional group will place different restrictions on the type of chemistry which can be carried out on the supported molecules.

A number of attempts have been made to link substrates to supports by linkers which are designed to be traceless, i.e. the linker leaves no feature on the final product. Traceless linkers are those that are not being used as a protecting group for a specific functional group, and that are removed from the product molecules as part of the process of releasing the molecules from the support. The traceless linkers reported so far (e.g Sucho Leiki I. Tetrahedron Lett., (1994), 35, 7307: Chenera B et. al., J. Am. Chem. Soc., (1995), 117, 11999: Plunkett, M. S. et. al., (1995), 60, 6006) have been developed for specific applications and are either of limited generality or require specific chemical synthesis of every variation of the first supported reagent, or leave behind a characteristic functional group that limits the diversity of the molecules produced. For instance, the existing examples of acid labile arylsilane linkers or reductively cleavable alkylthioether linkers are limited in scope and synthetically limited in accessibility. Acid labile arylsilane linkers are obtained by separate functionalisation or refunctionalisation of an aromatic ring of each linked substrate and after acid-induced cleavage of the linker every product contains a hydrogen atom at the position previously occupied by the silane functional group. The alkylthioether linkers similarly require a separate functionalisation or refunctionalisation of each linked substrate and cleavage of the thioether functional group that constitutes the link results in a reduction of the degree of functionality of the product.

Organometallic chemistry is a subset of chemistry dealing with the area of metals containing ligands bonded through a carbon atom. The area is extremely diverse due to the number of different interactions possible with the metal group, thus allowing any number of diverse compounds to be produced. One form of interaction between a metal and an organic group is in the form of a π-complex between an organic ligand having a π-bond, such as is present on an olefinic or an aromatic compound, and a transition metal. A characteristic of such complexes is that the bond between the transition metal and the organic group is formed to the π-orbitals of the organic group and not the σ-orbitals of the framework. Although the reactivity of the π-orbitals is thereby changed the connectivity of the framework of the organic group remains intact. Such π-bonded transition metal complexes constitute a well-known class of compounds that is described, for instance, in "Comprehensive Organometallic Chemistry" Wilkinson G., Stone G. A., and Abel E. W. Eds., Pergamon Press, 1982, Oxford, U.K. and in "Transition Metals in the Synthesis of Complex Organic Molecules" Hegedus L. S., University Science Books, 1994, Mill Valley, Calif., USA. Examples of such complexes with common organic compounds include (1) ("Comprehensive Organometallic Chemistry" Vol. 3, Chapter 26.2, Tables 10 and 11 1003–1005) and (2) ("Transition Metals in the Synthesis of Complex Organic Molecules" Chapter 7.3, 221).

Transition metal complexes serve as masking or protective groups for π-bonded ligands of organic compounds. Soluble π-bonded complexes of arenes with chromium(0), of alkynes with cobalt(0), dienes and enones with iron(0) and olefines with iron (+1) are well known and have been used as protective groups for organic groups during functional group manipulation.

In addition π-bonded transition metal complexes have been immobilised on solid polymer supports via a polymer attached phosphine ligand for use as catalysts in organic and polymer chemistry. The polymer support is needed so as to aid isolation of the catalyst from the reaction mixture.

We have now found that transition metal complexes can be used as traceless linkers of remarkable simplicity, generality, and utility. These transition metal complexes may be used to π-bond unsaturated organic substrate ligands, such as arenes, alkynes, alkenes, and dienes, to a support for use in combinatorial chemistry and MPS.

The invention is illustrated below.

A feature of the traceless linker illustrated is its versatility: not only can the transition metal attach to a wide variety of π-orbital containing substrates, to allow an enormous diversity of library components to be synthesised, but it can also be attached to a great variety of supports. The transition metal+linker ligand constitutes a "traceless" linker because no trace of the link in the form of a characteristic functional group remains on the chemically modified substrate molecule after it has been released, as the product, from the support. This is true also in cases where the original π-orbital containing framework (an unsaturated system) of the substrate ligand has itself been modified during the synthesis or cleavage of the product since the modification to the original π-orbital containing framework is a modification to the core or backbone of the molecule rather than to its functional groups. Therefore all the functional groups of a substrate supported in this way are available for diverse modification.

Presented as a first feature of the invention is the use of a transition metal complex as a traceless linker between a support and an unsaturated organic molecule by the formation of a π-complex bond between the transition metal and the unsaturated organic molecule and attaching of the transitional metal to the support before during or after the formation of the π-complex bond, which unsaturated organic molecule is then, preferably, a substrate for further chemical modification and eventual release from the traceless linker.

A further feature of the invention is a traceless linker system which comprises a transition metal complex attached to a support which is capable of forming a π-complex bond with an unsaturated organic molecule.

A further feature of the invention is a traceless linker system which comprises a transition metal complex attached to a support and an unsaturated organic molecule attached to the transition metal through a π-complex bond.

A further feature of the invention is a method of attaching to a support via a transition metal complex traceless linker an unsaturated organic molecule, which is then, preferable, a substrate for further chemical modification and eventual release from the transition metal complex, which method comprises one of the following alternative first steps:

(1) bonding the transition metal complex, which has bound to it through a π-complex bond the unsaturated organic substrate molecule, with the support, where the transition metal complex, support or both has a group capable of forming a bond, linker or interaction between the transition metal complex and the support;

(2) bonding the unsaturated organic substrate molecule with the transition metal complex, which is bound to the support, by forming a π-complex between the supported transition metal and the unsaturated organic substrate; or (3) converting an organic molecule which is σ- or π-bonded to the transition metal, which is bound to the support, to form a π-complex between the supported transition metal and the unsaturated organic substrate molecule.

Preferably specific preferred later steps include subsequent synthesis on the bound unsaturated organic substrate, where synthesis may be either by combinatorial chemistry or by multiple parallel synthesis techniques, and removal of the product from the support.

Thus formed is a π-substrate-transition metal-support complex in which the π-ligand, or ligands, is the substrate for a chemical reaction, and at least one of the other ligands of the complex is the linker group between the transition metal π-complex and the support. Examples of suitable complexes, where L is the linking ligand and S is the support, are:

1. π-Arene $Cr(CO)_2L$-S complexes as supported arene substrate.
2. $\eta^2$-Alkyne $Co_2(CO)_5L$-S complexes as supported alkyne substrate.
3. $\eta^2$-Alkene $FeCp(CO)L^+$-S and $\eta^4$-diene $Fe(CO)_2L$-S complexes as supported olefin substrate.

Where Cp=$\eta^5$-cyclopentadienyl anion

The support may be insoluble, such as a polymer or resin, soluble, such as a polyethylene glycol (PEG) which can be selectively precipitated as required, or fluorous phases, which show temperature dependent immiscibility with common organic solvents. It will be understood that it is possible to complex the unsaturated organic molecule to the transition metal at any stage, for example it may be convenient to build the transition metal complex onto the support prior to complexation with the unsaturated organic molecule or to complex the unsaturated organic molecule with the transition metal prior to attachment to the support. Alternatively the π-unsaturated organic molecule transition metal comple may be formed in situ by conversion of, for example, a σ-organic molecule transition metal complex.

The substrate ligand may be any unsaturated organic molecule containing at least one functional group that can be modified in a chemical synthesis and a π-orbital system that is capable of forming a π-complex with a suitable transition metal complex. The π-orbital system is preferably an integral part of the structural framework of both the substrate and the product rather than of one of the functional groups of the substrate or product.

The linking group can be any functional group capable of complexing with the transition metal and joining to the support. The linker group is preferably selected from those ligands known to form a strong bond to the transition metal. Suitable ligands include phosphines, phosphites, and isonitriles. A further embodiment of the reaction is that a single support bearing a common linking ligand can be used to support a wide variety of substrates through different transition metal complexes.

An additional embodiment of the invention is that the transition metal π-complex may itself take part in the chemical transformation. One example occurs where the formation of the complex of the unsaturated fragment (a π-system) of the substrate changes the reactivity of neighbouring functional groups to facilitate reactions that would otherwise be difficult to achieve; for instance the ready displacement of an aryl halide by diverse nucleophiles in π-arene $Cr(CO)_2L$ complexes. A further example occurs where the unsaturated fragment (a π-system) of the substrate ligand itself undergoes a chemical reaction to produce a new unsaturated fragment (a π-system) of a modified substrate;

for instance in the reaction of $[\eta^5\text{-dienylFe(CO)}_2\text{L}]^+$ complexes with carbanions to give $\eta^4\text{-dieneFe(CO)}_2\text{L}$ complexes. A further example occurs where the unsaturated fragment (a π-system) of the substrate ligand itself undergoes a chemical reaction to produce a modification of the unsaturated fragment that no longer complexes to the supported transition metal complex so that concomitant release of the product ligand occurs to give the unsupported product; for instance in the Paulson-Khand reaction of $\eta^2$-alkyne $\text{Co}_2(\text{CO})_5\text{L}$ complexes to give cyclopentenones.

A suitable transition metal is one capable of forming a cleavable stable π-complex contemporaneously with the π-orbital containing substrate and other ligands, at least one of which (the linker ligand) is able to be covalently attached to the solid support. The preferred transition metal varies according to the nature of the substrate ligand. Factors affecting the choice of suitable transition metal are known to those skilled in the art and are described inter alia in "Comprehensive Organometallic Chemistry" Wilkinson G., Stone G. A., and Abel E. W. Eds., Pergamon Press. 1982, Oxford, U.K.

Another additional embodiment of the invention is that when a transition metal complex linked to the support contains at least one exchangeable ligand other than the linker and substrate ligands, this exchangeable ligand can be replaced in part at each stage of the chemical modification of the substrate ligand by treatment with trace quantities of a tagging ligand. The unique combination of tagging ligands thus specifies the chemical history of the substrate linked to the support and acts as a label for e.g. resin beads in combinatorial split synthesis.

The tagging ligands are chosen from a set of similar but diverse compounds such as triaryl phosphines or halogenated alkyl or aryl phosphites, where each tagging molecule is unique to each of the different chemical modification steps used in the overall synthesis.

The tagging techniques described above may be practised not only on the transition metal complex linking the substrate to the support but to additional transition metal complexes on the support added exclusively for tagging. Alternatively the tagging techniques described above may be used alongside other linker techniques. Suitable tagging ligands are detectable and identifiable by mass spectrometry.

Presented as a further feature of the invention is a method for tagging a support within a chemical synthesis comprising for each reaction step desired to be labelled contacting a transition metal complex containing an exchangeable ligand bound to the support with a tagging ligand unique for the reaction being performed.

Presented as a further feature of the invention is a method for tagging a support within a chemical synthesis comprising for each reaction step desired to be labelled contacting a transition metal complex with a reactive group capable of making an analysable modification on one of the ligands of the transition metal complex unique for the reaction being performed.

It will be understood that the tagging reagents, whether a tagging ligand or reactive group, are introduced in such a way that only a small fraction of the sites that may be tagged are modified in any single step. Used in this way several different tagging reagents may be added separately and sequentially to unambiguously identify each of a sequence of several chemical reactions without any of the tagging reagents significantly interfering with the effectiveness of any of the other tagging reagents or with the chemistry being carried out on the supported π-complex of the substrate.

A cleavable stable π-complex is one in which the complex of the substrate ligand and the transition metal is stable to storage and use and from which the product ligand can be released. Preferably the unsaturated fragment (a π-system) will be unchanged. Factors affecting the choice of suitable cleavable complexes are known to those skilled in the art and are described inter alia, in "Comprehensive Organometallic Chemistry" Wilkinson G., Stone G. A., and Abel E. W. Eds., Pergamon Press, 1982, Oxford, U.K.

The product ligand (unsaturated organic molecule with modified functional groups) may be cleaved from the complex to give the product by any effective method that does not damage the structural integrity of the product. Suitable methods include thermal, photochemical, and oxidative cleavage.

The substrate transition metal π-complex is located on the surface or throughout the support in such a way that it is accessible to the constituents of a reaction that is to be carried out on the substrate ligand.

A-π-bonded transition metal complex with an exchangeable ligand can be preformed and attached to a supported ligand to give a supported π-bonded transition metal complex, by a simple process of ligand exchange well known to those skilled in the art.

A transition metal complex with exchangeable ligands can be attached to a supported ligand to give a supported transition metal complex with exchangeable ligands and these ligands can be replaced with the substrate ligand (unsaturated organic molecule) with an unsaturated fragment (a π-system), another simple process of ligand exchange well known to those skilled in the art.

A-π-bonded transition metal complex with a functionalised linking ligand can be preformed and attached to a support by refunctionalisation of the functionalised linking ligand to give a supported π-bonded transition metal complex, for instance by coupling a carboxy functionalised linking ligand to an amino-functionalised support by amide bond formation.

A supported transition metal complex containing a ligand may be chemically modified so that the ligand is converted into a π-bonded substrate ligand of a π-bonded transition metal complex; for instance in the conversion by Doetz reaction of supported σ-carbeneCr(CO)$_4$L complexes into π-arene Cr(CO)$_2$L complexes of supported arenes (σ-complex to π-complex).

A supported transition metal complex containing a π-bonded ligand may be chemically modified so that the π-bonded ligand is converted into a π-bonded substrate ligand; for instance in the conversion of $[\eta^5\text{-dienylFe(CO)}_2\text{L}]^+$ complexes into $\eta^4\text{-dieneFe(CO)}_2\text{L}$ complexes (π-bonded complex to another π-bonded complex).

EXAMPLES

Photolysis of Diphenylphosphinopolystyrene with Tricarbonyl(arene) Chromium Complex Diphenylphosphinopolystyrene[1], (3 mmol g$^{-1}$, 1.59 g, 4.77 mmol) was stirred in tetrahydrofuran (THF) (350 mL) for 1 hour before addition of tricarbonyl[4-(p-methoxyphenyl)butan-2-one]chromium (1.65 g, 5.25 mmol). The mixture was irradiated (125 W Phillips Hg-vapour lamp) for 3 hours, and then allowed to react in the dark for a further 1 hour. The reaction mixture was transferred by cannula into 1 L round-bottomed flask, and the solid allowed to settle. The supernatant solvent was removed by cannula, and the residual solid washed with THF (2×100 mL). The solid was then dried in vacuo to give the polymer supported dicarbonyl[4-(p-methoxyphenyl) butan-2-one]chromium complex as a brown powder (2.3 g). $v_{max}$ (Nujol mull)/cm$^{-1}$ 2059(m), 1983(w) and 1933(s) [•PPh$_2$Cr(C≡O)$_5$], 1870(s) and 1802(s) [•-PPh$_2$Cr(C≡O)$_2$Ar]$^2$, 1710 (C=O); $\delta_P$ (202.4 MHz, CDCl$_3$) 90 [•PPh$_2$Cr(CO)$_2$Ar, 40%], 56 [•-PPh$_2$Cr(CO)$_5$. 22%], 29 [•-P(O)Ph$_2$, 11%),31 5 (•-PPh$_2$, 27%).

[1]. represented as • PPh$_2$. Available from Aldrich as 'triphenylphosphine, polymer supported', reference 36, 645-5. Polymer is polystyrene, cross-linked with 2% divinylbenzene.

[2]. see Table 1 for comparison of data with analogous compounds free of a polymer support.

Reduction of Ketone

The polymer supported dicarbonyl[4-p-methoxyphenyl) butan-2-one]chromium complex described above (40% of 3 mmol g$^{-1}$=1.2 mmol g$^{-1}$; 1 g, 1.2 mmol) was stirred in THF (80 mL) for 1 hour, and then cooled to 0° C. Lithium aluminium hydride (0.137 g, 3.6 mmol) was dissolved in THF (10 mL), and the solution added dropwise to the polymer suspension via cannula. The mixture was allowed to warm to room temperature, and stirred for 16 hours. Ethyl acetate (10 mL) was cautiously added, followed by water (10 mL), and the mixture allowed to settle. The supernatant liquid was removed by cannula, and the remaining solid washed with THF (2×20 mL) and diethyl ether (20 mL). The solid was dried in vacuo, to give the polymer supported dicarbonyl[4-p-methoxyphenyl)butan-2-ol]chromium complex as a dark yellow powder (0.930 g). $v_{max}$(Nujol mull)/cm$^{-1}$ 2060(vw), 1929(vw) [• PPh$_2$Cr(C≡O)$_5$], 1876(s) and 1814(s) [• PPh$_2$Cr(C≡O)$_2$Ar], complete absence of ketone at 1710; $\delta_P$ (202.4 MHz, CDCl$_3$) 86 [• PPh$_2$Cr(CO)$_2$Ar, 24%], 54 [•-PPh$_2$Cr(CO)$_5$, trace], 22 (•-P(O)Ph$_2$, 21%), –21 (•-PPh$_2$, 55%).

Decomplexation Using Pyridine

The polymer supported dicarbonyl[4-(p-methoxyphenyl) butan-2-ol]chromium complex isolated above loaded (24%) diphenylphosphinopolystyrene (24% of 3 mmol g$^{-1}$=0.72 mmol g$^{-1}$, 0.500 g, 0.36 mmol) was added to pyridine (10 mL), the mixture was degassed, and heated at reflux under a nitrogen atmosphere for 2 hours, during which time the mixture became bright red. The mixture was allowed to cool, and the solid to settle out. Supernatant liquid was removed via cannula, and the residual solid was washed successively with THF (2×20 mL) and diethyl ether (20 mL). The organic washings were concentrated in vacuo and washed through a short pad of silica with diethyl ether. Ether was removed by evaporation to leave 4-(p-methoxyphenyl)butan-2-ol as a colourless oil (≧95% purity by $^1$H-nmr spectroscopy; 60 mg, 0.33 mmol, 92%). $\delta_H$ (270 MHz, CDCl$_3$) 7.14 [2H, d, J 8 Hz, CHC(OMe)CH], 6.85 [2H, d, J 8 Hz, CHC(R)CH], 3.83 (1H, m, CHOH), 3.81 (3H, s, OCH$_3$), 2.66 [2H, m, CH$_2$CH(OH)], 1.76 (3H, m, ArCH$_2$ and OH), 1.24 [3H, d, J 6 Hz, CH(OH)CH$_3$].

| Subtance | $v_{max}$.Cm$^{-1}$ | $^{31}$P | Ref. |
|---|---|---|---|
| •-PPh$_2$ | | –6.3 | J. Org. Chem., 1983, 48, 326 |
| •-PPh$_2$=O | | 28.8 | J. Org. Chem., 1983, 48, 326 |
| Cr(CO)$_5$PPh$_3$ | 2065, 1980, 1940 | 55.3 | J. Am. Chem. Soc., 1967, 89, 5573 |
| | | 58 | J. Organomet. Chem., 1994, 468, 143 |
| Cr(CO)$_2$PPh$_3$C$_6$H$_5$OMe | 1886s, 1827s | 91.9 | Polyhedron, 1988, 7, 1377 |
| Cr(CO)$_2$PPh$_3$C$_6$H$_5$NMe$_2$♦ | 1869, 1806 | 93.5 | Polyhedron, 1988, 7, 1377 |
| Cr(CO)$_2$PPh$_3$C$_6$H$_5$CHO♦ | 1917, 1861 | 84.9 | Polyhedron, 1988, 7, 1377 |
| MeOC$_6$H$_4$(CH$_2$)$_2$COMe. Cr(CO)$_3$ | 1972vs, 1903vs and 1710s | | Synthesised as part of this work |

♦Included to represent extremes of ring electron density.

General Experimental

Reactions under nitrogen were performed using standard vacuum line techniques. Diethyl ether was dried over sodium wire and tetrahydrofuran was distilled from sodium benzophenone ketyl. Unless otherwise stated, reagents were obtained from commercial sources. IR spectra were obtained on a Perkin-Elmer 1710 FTIR spectrometer instrument. NMR spectra were recorded at room temperature on JEOL GSX 270 (270 MHz $^1$H) and Briker DRX 500 (500.0 MHz $^1$H, 202.4 MHz $^{31}$P) spectrometers. J values are given in Hz.

Figure 1:
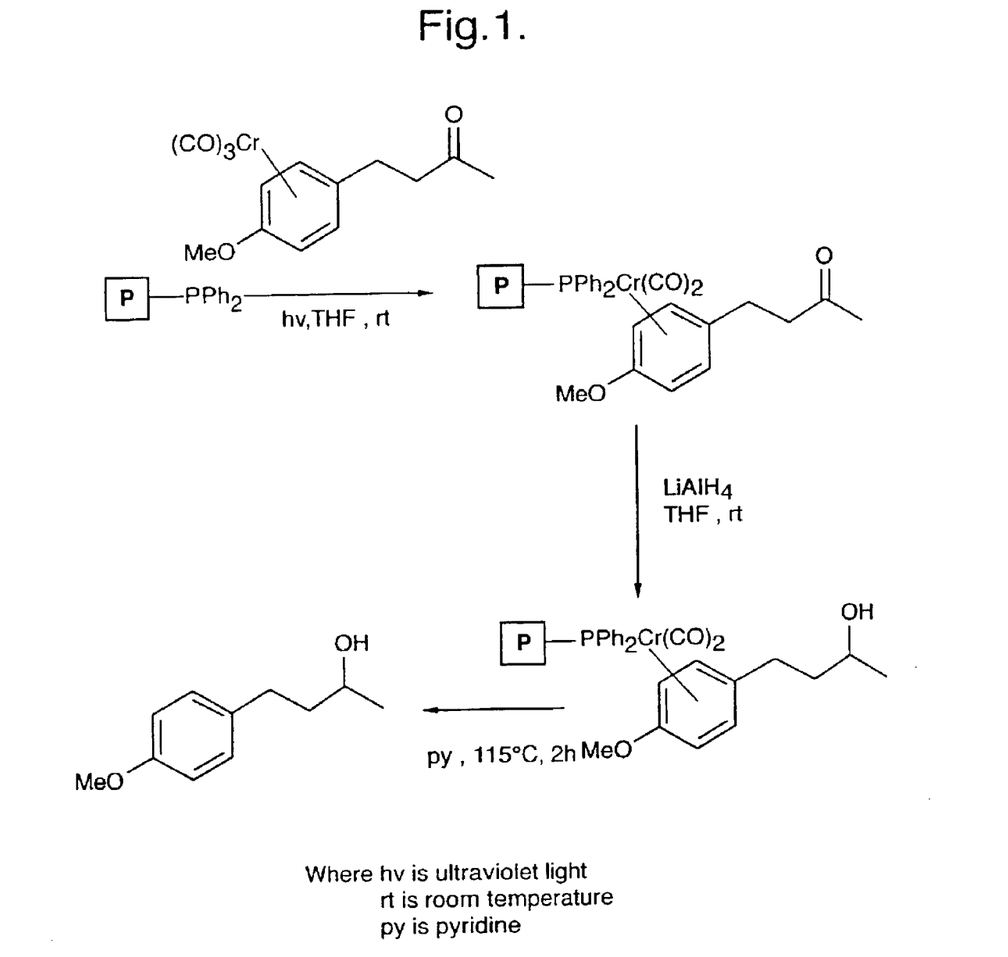
FIG. 1. Illustrates joining of a π-bonded transition metal substrate complex to a support via ligand exchange, a subsequent reaction step to the substrate ligand and later release of the product ligand from the transition metal polymer complex.
Figure 2:
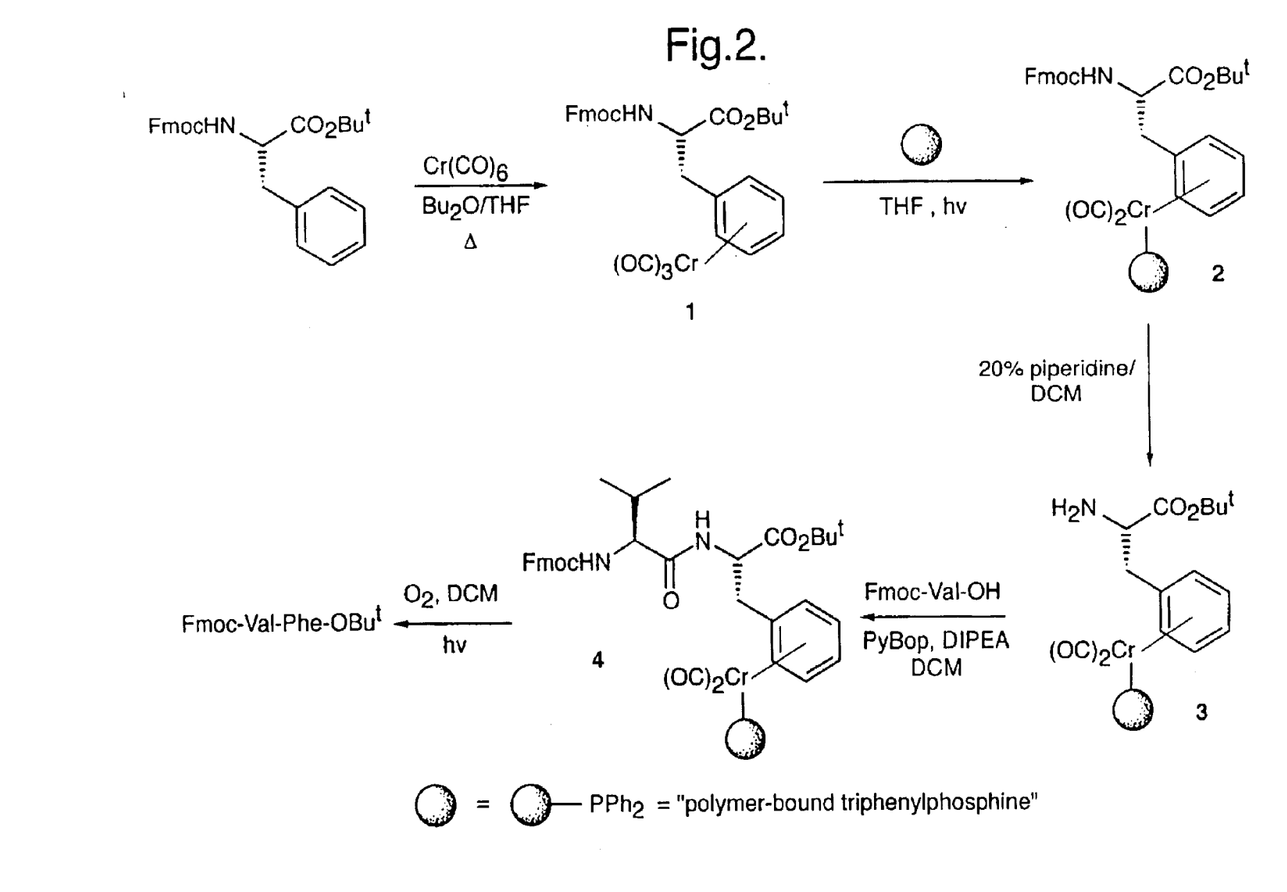

Experimental Details for Chromium Peptide Linker—FIG. 2

Tricarbonyl(Fmoc-Phe-OBu$^t$)chromium(0)
[FIG. 2, 1]

Fmoc-Phe-OBu$^t$ (2 g, 4.51 mmol), hexacarbonylchromium(0) (1.04 g, 4.74 mmol), anhydrous dibutyl ether (40 cm$^3$) and anhydrous THF (10 cm$^3$) were combined and the mixture was thoroughly deoxygenated and heated to reflux under nitrogen for 40 h. The resulting red solution was cooled and the solvent was evaporated at reduced pressure. Column chromatography (SiO$_2$, gradient elution hexane:diethyl ether 2-100%) effected purification of the following product mixture:

i) (5% diethyl ether): red solid tricarbonyl (dibenzofulvene)chromium(0) (225 mg, 0.72 mmol, 16%); mp 135° C. dec., [Found: m/z (M) 314.0037, C$_{17}$CrH$_{10}$O$_3$ requires 314.0035]; $v_{max}$(Et$_2$O)/cm$^{-1}$ 1969vs, 1904s (C≡O); $\delta_H$ (300 MHz)(CDCl$_3$) 5.39–5.53 (2 H, m, CCH$_2$), 5.92–6.10 (4 H, m, ArCr(CO)$_3$), 7.25–7.68 (4 H, m, Ar); m/z (FAB+) 314 (M, 65%),286 (M—CO, 23%), 258 (M—2CO, 68%), 230 (M—3CO, 31%), 178 (M—Cr—3CO, 36%);

ii) (5–20% diethyl ether): yellow uncomplexed Fmoc-Phe-OBu$^t$ (340 mg, 0.77 mmol, 17%);

iii) (100% diethyl ether): product complex as a crystalline yellow foam (820 mg, 1.42 mmol, 31%); mp 82–84° C.; [Found: m/z (M—3CO) 495.1519, $C_{28}CrH_{29}NO_4$ requires 495.1502]; $[\alpha]^{20}_D$+16.9° (c=1.0, DCM); $v_{max}$(DCM)/cm$^{-1}$ 1969vs, 1892vs (C≡O), 1723m [C(=O)OBu$^t$]; $\delta_H$ (360 MHz)(CDCl$_3$) 1.46 (9 H, s, OC(CH$_3$)$_3$), 2.6–2.9 (2 H, m, CH$_2$Ph), 4.18 (1 H, m, OCHH), 4.33–4.44 (2 H, m, OCHH, OCH$_2$CH), 4.58 (1 H, dd, J 7, 11, NCHCO$_2$), 4.92 (1 H, d, J 6, NH), 5.09 (5 H, m, H-2, H-3, H4, H-5, H-6), 7.30–7.79 (8 H, m, H-9, H-10, H-11, H-12, H-15, H-16, H-17, H-18); $\delta C\{^1H\}$ (90 MHz)(CDCl$_3$) 28.1 (OC(CH$_3$), 38.3 ([Cr]—PhCH$_2$), 47.3 (C-7), 55.2 (NHCHCO$_2$), 66.6 (CO$_2$CH$_2$), 83.5 (OC(CH$_3$)$_3$), 90.7, 92.9, 93.4, 93.4, 93.7 (C-2, C-3, C4, C-5, C-6), 107.0 (C-1), 120.0, 120.1 (C-12, C-15), 124.9, 125.1, 127.2, 127.9, 127.9, 128.6 (C-9, C-10, C-11, C-16, C-17, C-18), 141.4 (C-13, C-14), 143.6, 143.8 (C-8, C-19), 155.4 (NHCO$_2$), 169.7 (NCHCO$_2$), 232.7 (Cr(CO)$_3$); m/z (FAB+) 579 (m, 1.4%), 524 (M—2CO+H, 2.6%), 495 (M—3CO, 33%), 439 (M—3CO—CMe$_3$+H, 8%), 179 (dibenzofulvene+H, 30%), 147 (PhCH$_2$CHNH+H, 28%), 91 (PhCH$_2$, 49%), 73 (OCMe$_3$, 100%).

Dicarbonyl(Fmoc-Phe-OBu$^t$)(polymer-PPh$_2$) chromium(0) [FIG. 2, 2]

To a suspension of polymer-bound triphenylphosphine (450 mg, 0.72 mmolP) at ambient temperature in anhydrous THF (200 cm$^3$) was added tricarbonyl(Fmoc-Phe-OBu$^t$) chromium(0) (500 mg, 0.86 mmol). Under constant nitrogen agitation, the yellow mixture was subjected to periodic irradiation (4×10 min) over a 48 h period. The resulting deep red beads were filtered, washed thoroughly with alternate aliquots of THF and diethyl ether and dried in vacuo to afford the product resin (732 mg, 63% loading by mass, 0.69 mmol[Fmoc-Phe-OBu$^t$]g$^{-1}$); $v_{max}$(Nujol)/cm$^{-1}$ 2005vw, 1936vw [polymer-PPh$_2$Cr(C≡O)$_5$, polymer-(PPh$_2$)$_2$Cr (C≡O)$_4$], 1874vs, 1828s [polymer-PPh$_2$Cr(C≡O)$_2$(Ar)], 1718m [C(=O)OBu$^t$]; $\delta_P$ (202.5 MHz)(D$_2$O capillary lock) –3.3 (polymer-PPh$_2$, 12%), 27.4 [polymer-P(O)Ph$_2$, 17%], 58.0 [polymer-PPh$_2$Cr(CO)$_5$, 2%], 78.4 [polymer-(PPh$_2$)$_2$Cr (CO)$_4$, 4%], 93.2 [polymer-PPh$_2$Cr(CO)$_2$(Fmoc-Phe-OBu$^t$), 70%].

Dicarbonyl(H-Phe-OBu$^t$(polymer-PPh$_2$)chromium (0) [FIG. 2, 3]

To a suspension of dicarbonyl(Fmoc-Phe-OBu$^t$)(polymer-PPh$_2$)chromium(0) (250 mg, 0.17 mmol[Fmoc-Phe-OBu$^t$]) in anhydrous DCM (8 cm$^3$) at ambient temperature was added piperidine (2 cm$^3$). After 20 mins under constant nitrogen agitation, the beads were filtered and washed with alternate aliquots of DCM and diethyl ether. The process was repeated: re-suspension in 20% piperidine/DCM (10 cm$^3$) for 10 mins, filtration and washing as before afforded red beads of the product resin, taken directly to the next coupling step; $v_{max}$(Nujol)/cm.$^{-1}$ 1883vs, 1832s [Cr (C≡O)$_2$], 1720m [C(=O)OBu$^t$].

Dicarbonyl(Fmoc-Val-Phe-OBu$^t$)(polymer-PPh$_2$) chromium(0) [FIG. 2, 4]

A solution of diisopropylethylamine (0.152 cm$^3$, 0.87 mmol) and Fmoc-Val-OH (148 mg, 0.44 mmol) in anhydrous DCM (2 cm$^3$) was added to a suspension of dicarbonyl (H-Phe-OBu$^t$)(polymer-PPh$_2$)chromium(0) in anhydrous DCM (2 cm$^3$) at ambient temperature. PyBop (227 mg, 0.44 mmol) was added immediately and the mixture was left under constant nitrogen agitation for 6 h. The resulting red beads were filtered, washed thoroughly with alternate aliquots of DCM, methanol and diethyl ether and dried in vacuo to afford the product resin (265 mg, 0.61 mmol[Fmoc-Val-Phe-OBu$^t$]g$^{-1}$); $v_{max}$(Nujol)/cm$^{-1}$ 1883vs, 1832s [Cr (C≡O)$_2$], 1724m [C(=O)OBu$^t$], 1680m [CH(C=O)N]; $\delta_P$ (145.8 MHz)(D$_2$O capillary lock) –4.8 (polymer-PPh$_2$, 8%), 26.2 [polymer-P(O)Ph$_2$, 20%], 57.8 [polymer-PPh$_2$Cr(CO)$_5$, 3%], 75.1 [polymer-(PPh$_2$)$_2$Cr(CO)$_4$, 6%], 91.8 [polymer-PPh$_2$Cr(CO)$_2$(Fmoc-Val-Phe-OBu$^t$), 63%].

Fmoc-Val-Phe-OBu$^t$

Dicarbonyl(Fmoc-Val-Phe-OBu$^t$)(polymer-PPh$_2$) chromium(0) (100 mg, 0.065 mmol[Fmoc-Val-Phe-OBu$^t$]) was suspended in DCM (15 cm$^3$) in a 25 cm$^3$ round-bottomed flask equipped with a condenser and CaCl$_2$ drying tube and stirred at ambient temperature in air under white light (100 W) for 48 h. The resulting brown suspension was filtered through celite and the polymeric residue was washed with DCM. The combined filtrate and washings were concentrated at reduced pressure to afford the colourless dipeptide (36 mg, 0.065mmol, 99%); $v_{max}$(neat)/cm$^{-1}$ 1732vs [C(=O)OBu$^t$], 1692vs [C(=O)N], 1657vs [OC(=O)N]; $\delta_H$ (360 MHz/CDCl$_3$) 0.94 (6 H, m, CH(CH$_3$)$_2$), 1.39 (9 H, s, C(CH$_3$)$_3$), 2.10 (1 H, q, J 7, CH(CH$_3$)$_2$), 3.08 (2 H, d, J 6, ArCH$_2$), 4.06 (1 H, m, Val αH), 4.23 (1 H, dd, J 7, OCHH, OCHH or OCH$_2$CH), 4.33 (1 H, dd, J 7, 7, OCHH, OCHH or OCH$_2$CH), 4.46 (1 H, dd, J 7, 10, OCHH, OCHH or OCH$_2$CH), 4.78 (1 H, m, Phe αH), 5.51 (1 H, d, J 9, NH), 6.43 (1 H, d, J 8, NH), 7.14–7.78 (13 H, m, Ar); $\delta_C$ (90 MHz)(CDCl$_3$) 17.9, 19.2 (CH(CH$_3$)$_2$), 28.0 (C(CH$_3$)$_3$), 31.4 (CH(CH$_3$)$_2$), 38.2 (PhCH$_2$), 47.2 (C-7), 53.7 (Phe αC), 60.3 (Val αC), 67.1 (CO$_2$CH$_2$), 82.5 (C(CH$_3$)$_3$), 120.0 (C-12, C-15), 125.2, 125.2, 127.1, 127.1, 127.8, 128.5, 129.5 (C-9, C-10, C-11 , C-16, C-17, C-18, C-2, C-3, C4, C-5, C-6), 136.0 (C-1), 141.4 (C-13, C-14), 143.9 (C-8, C-19), 156.4 (NCOO), 170.3, 170.8 (Val CO, Phe CO).

Figure 3:
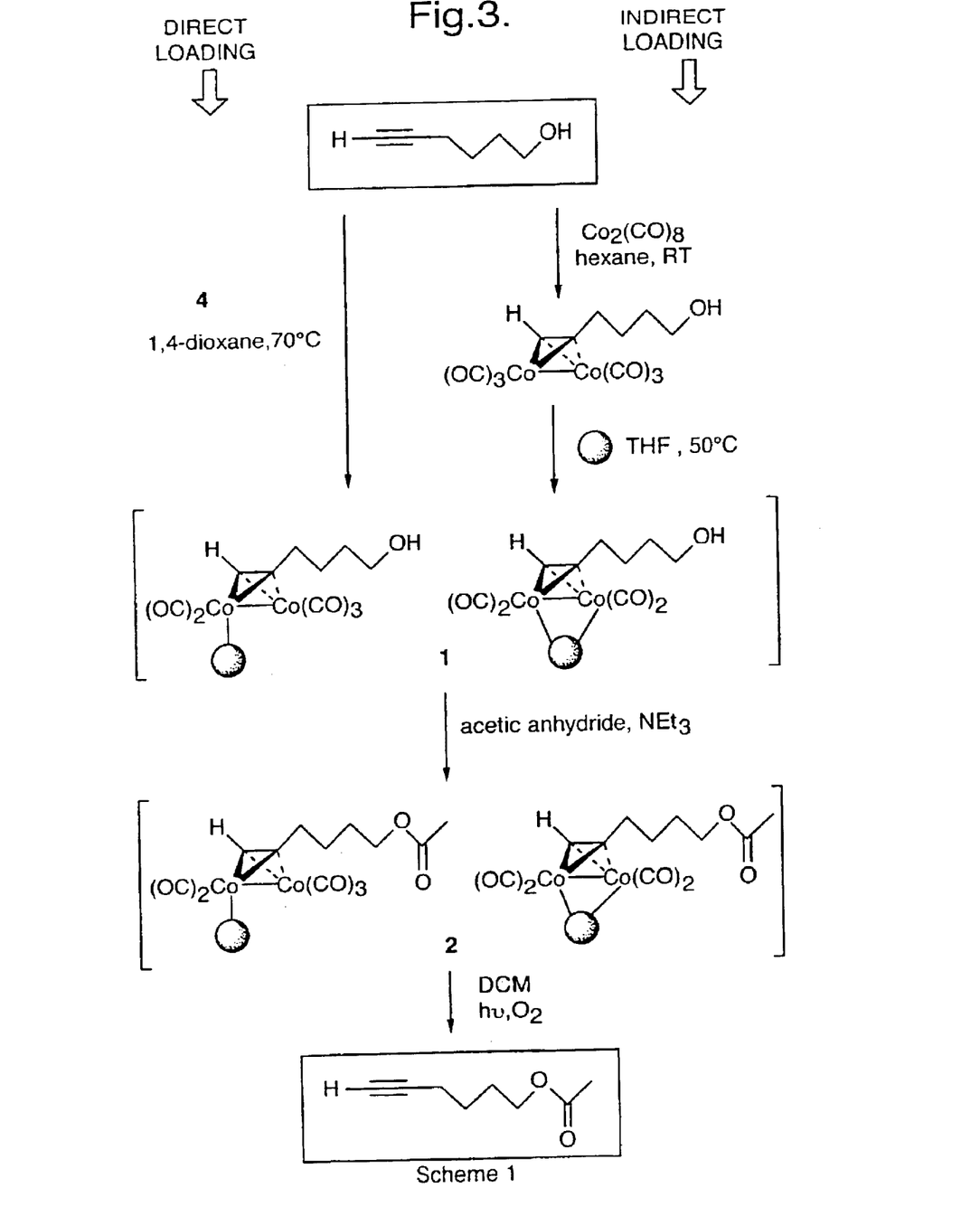

Experimental Details for Cobalt Linker—FIG. 3

(A) Indirect Method (Unsaturated Organic Molecule Transition Metal Complex Formation First then Attachment to Support)

Polymer-(PPh$_2$)$_n$(CO)$_{6-n}$Co$_2$(5-hexyn-1-ol) [FIG. 3, Scheme 1, 1]

Polymer-bound triphenylphosphine (1 g, 1.6 mmolP) was suspended at ambient temperature in anhydrous THF (10 cm$^3$) and a solution of hexacarbonyl(5-hexyn-1-ol)cobalt(0)

(1.2 g, 3.2 mmol) was added. The mixture was heated to 50° C. under constant nitrogen agitation for 4 h. The resulting deep purple beads were filtered, washed with alternate aliquots of THF and diethyl ether until the filtrate became colourless, and dried in vacuo to afford the product resin (1.52 g, 0.94±0.02 mmol[5-hexyn-1-ol]g$^{-1}$); $v_{max}$(Nujol)/cm$^{-1}$ 2055s, 1998vs, 1979ssh, 1950s (C≡O); $\delta_P$ (145.8 MHz)(D$_2$O capillary lock) 25.6 [polymer-P(O)Ph$_2$, 20%], 55.5 [polymer-(PPh$_2$)$_n$Co$_2$(CO)$_{6-n}$(5-hexyn-1-ol), 80%].

(a) Esterification

Polymer-(PPh$_2$)$_n$(CO)$_{6-n}$Co$_2$(5hexyn-1-yl acetate)
[FIG. 3, Scheme 1, 2]

Polymer-(PPh$_2$)$_n$(CO)$_{6-n}$Co$_2$(5-hexyn-1-ol) [300 mg, 0.28 mmol(5-hexyn-1-ol)] was suspended at ambient temperature in anhydrous THF (10 cm$^3$) under constant nitrogen agitation. Triethylamine (2.5 cm$^3$) and acetic anhydride (1.5 cm$^3$) were added sequentially. After 20 h at ambient temperature, the resulting deep purple beads were filtered, washed thoroughly with alternate aliquots of THF and diethyl ether and dried in vacuo to afford the product resin (325 mg, 0.87±0.02 mmol[5-hexyn-1-yl acetate]g$^{-1}$); $v_{max}$(Nujol)/cm$^{-1}$ 2055s, 1994vs, 1981ssh, 1950s (C≡O), 1734m [O(C=O)CH$_3$]; $\delta_P$ (145.8 MHz)(D$_2$O capillary lock) 24.7 [polymer-P(O)Ph$_2$, 24%], 54.3 [polymer-(PPh$_2$)$_n$Co$_2$(CO)$_{6-n}$(5-hexyn-1-yl acetate), 76%).

5-hexyn-1-yl acetate

Polymer-(PPh$_2$)$_n$(CO)$_{6-n}$Co$_2$(5-hexyn-1-yl acetate) (120 mg, 0.104 mmol[5-hexyn-1-yl acetate]) was suspended in DCM (15 cm$^3$) in a 25 cm$^3$ round bottomed flask equipped with a condenser and CaCl$_2$ drying tube and stirred at ambient temperature in air under white light (100 W) for 72 h. The resulting brown suspension was filtered through celite and the polymeric residue was washed with DCM. The combined filtrate and washings were concentrated at reduced pressure to afford the oily colourless product (12 mg, 0.09 mmol, 61%); $v_{max}$(neat)/cm$^{-1}$ 3683, 2931, 2359, 2249, 1732, 1367, 1242, 909, 650; $\delta_H$ (400 MHz)(CDCl$_3$) 1.50–1.73 (4 H, m, CH$_2$CH$_2$CH$_2$O), 1.90 (1 H, t, J 3, HCCCH$_2$), 1.98 (3 H, s, COCH$_3$), 2.17 (2H, td, J 3, 7, HCCCH$_2$), 4.02 (2 H, t, J 7, CH$_2$O); $\delta_C${$^1$H} (90MHz)(CDCl$_3$) 18.1 (CCCH$_2$), 21.0 (COCH$_3$), 25.0 (CH$_2$CH$_2$OCO), 27.7 (CCCH$_2$CH$_2$), 64.0 (CH$_2$OCO), 68.8 (HCCCH$_2$), 83.9 (HCCCH$_2$), 171.2 (CO).

(b) Oxidation

Polymer-(PPh$_2$)$_n$(CO)$_{6-n}$Co$_2$(5-hexyn-1-al)
[FIG. 3, Scheme 2, 3]

Polymer-(PPh$_2$)$_n$(CO)$_{6-n}$Co$_2$(5-hexyn-1-ol) (500 mg, 0.47 mmol[5-hexyn-1-ol]) was suspended at ambient temperature in anhydrous DCM (5 cm$^3$) under constant nitrogen agitation. Dimethylsulfoxide (3 cm$^3$) and triethylamine (515 mg, 0.71 cm$^3$, 5.1 mmol) were added sequentially, followed by a solution of sulfur trioxide pyridine complex (405 mg, 2.55 mmol) in dimethylsulfoxide (2 cm$^3$). After 7 h at ambient temperature, the resulting deep purple beads were filtered, washed thoroughly with alternate aliquots of dimethylsulfoxide, DCM and diethyl ether and dried in vacuo to afford the product resin (495 mg, 0.85 mmol (5-hexyn-1-al]g.$^{-1}$); $v_{max}$(Nujol)/cm$^{-1}$ 2056s, 1996vs, 1980ssh, 1951s (C≡O), 1723m (CHO); $\delta_P$ (145.8 MHz) (D$_2$O capillary lock) 24.6 [polymer-P(O)Ph$_2$, 30%], 54.1 [polymer-(PPh$_2$)$_n$Co$_2$(CO)$_{6-n}$(5-hexyn-1-al), 70%].

5-Hexyn-1-al

Decomplexation of the alkynyl aldehyde was effected in a procedure identical to that described for the alkynyl ester above. Careful evaporation of the filtrate and washings afforded the colourless volatile product (6 mg, 0.06 mmol, 18%); $v_{max}$(neat)/cm$^{-1}$ 3688, 3310, 2929, 2246, 1723, 1682, 1931, 1265, 643; $\delta_H$ (360 MHz)(CDCl$_3$) 1.5–1.7 (2 H, m, CH$_2$CH$_2$CHO), 1.92 (1 H, t, J 3, HCCCH$_2$), 2.21 (2 H, dt, J 3, 7, HCCCH$_2$), 2.55 (2 H, dt, J 1, 7, CH$_2$CHO), 9.81 (1 H, t, J 1, CHO); $\delta_C${$^1$H} (90 MHz)(CDCl$_3$), 17.8, 20.8 (CCCH$_2$CH$_2$), 42.6 (CH$_2$CHO), 69.4 (CCCH$_2$), 79.8 (HCCCH$_2$), 201.8 (CHO).

(B) Direct Method
(Unsaturated Organic Molecule Completed with Transition Metal Already Attached to the Support)

Polymer-(PPh$_2$)$_n$Co$_2$(CO)$_{8-n}$ [FIG. 3, Scheme 3, 4]

Polymer-bound triphenylphosphine (2 g, 3.2 mmolP) was suspended at ambient temperature in anhydrous THF (10 cm$^3$) and octacarbonyldicobalt(0) (2.2 g, 6.4 mmol) was added. After 1.5 h under constant nitrogen agitation, the mixture was filtered and washed with alternate aliquots of THF and diethyl ether until the filtrate became colourless. Subsequent suspension in chloroform allowed separation by decantation of a small amount of inorganic material from the deep purple beads which were dried in vacuo to afford the product complex (2.37 g, 0.91±0.06 mmol[Co$_2$(CO)$_x$]g$^{-1}$); $v_{max}$(Nujol)/cm$^{-1}$ 2074w, 2012msh, 1995s, 1985msh, 1955w, 1880vs; $\delta_P$ (145.8 MHz)(D$_2$O capillary lock) 32 [polymer-P(O)Ph$_2$, 25%], 62 [polymer-(PPh$_2$)$_n$Co$_2$(CO)$_{8-n}$, 75%].

Polymer-(PPh$_2$)$_n$(CO)$_{6-n}$Co$_2$(5-hexyn-1-ol)
[FIG. 3, Scheme 1, 1]

To a suspension of polymer-(PPh$_2$)$_n$(CO)$_{8-n}$Co$_2$ (400 mg, 0.36 mmol[Co$_2$(CO)$_x$]) in anhydrous dioxane (10 cm$^3$) was added 5-hexyn-1-ol (254 mg, 0.29 cm$^3$, 2.6 mmol). After 2 h constant nitrogen agitation at 70° C., the deep purple beads were filtered, washed thoroughly with alternate aliquots of THF and diethyl ether and dried in vacuo to afford the product complex (408 mg, 0.43±0.09 mmol[5-hexyn-1-ol] g$^{-1}$); $v_{max}$(Nujol)/cm$^{-1}$ 2055w, 2009s, 1967ssh, 1948vs, 1930ssh; $\delta_P$ (145.8 MHz)(D$_2$O capillary lock) −5 (polymer-PPh$_2$, 20%), 25 [polymer-P(O)Ph$_2$, 50%], 55 [polymer (PPh$_2$)$_n$Co$_2$(CO)$_{8-n}$, 30%].

For acetylation and decomplexation of the product alkynyl ester the procedures were identical to those employed for the indirect method.

What is claimed is:

1. A method for making a metal complex as a traceless linker between a support and an unsaturated organic molecule comprising the formation of a π-complex bond between a transition metal and the unsaturated organic molecule and attaching of the transitional metal to the support before, during or after the formation of the π-complex bond by a linking ligand that is a phosphine, phosphite or isonitrile; wherein the transition metal is cobalt or chromium.

2. A traceless linker system which comprises a transition metal complex attached to a support which is capable of forming a π-complex bond with an unsaturated organic molecule; wherein the transition metal is attached to the solid support by a linking ligand that is a phosphine, phosphite or isonitrile, and the transition metal is cobalt or chromium.

3. A traceless linker system which comprises a transition metal complex attached to a support and an unsaturated organic molecule attached to the transition metal through a η-complex bond; wherein the transition metal is attached to the solid support by a linking ligand that is a phosphine, phosphite or isonitrile, and the transition metal is cobalt or chromium.

4. A method of attaching to a support via a transition metal complex traceless linker an unsaturated organic molecule, which method comprises one of the following alternative first steps:

(1) bonding the transition metal complex, which has bound to it through a π-complex bond the unsaturated organic substrate molecule, with the support, where the transition metal complex, support or both has a group capable of forming a bond, linker or interaction between the transition metal complex and the support;

(2) bonding the unsaturated organic substrate molecule with the transition metal complex, which is bound to the support, by forming a π-complex between the supported transition metal and the unsaturated organic substrate;

(3) converting an organic molecule which is σ- or π-bonded to the transition metal, which is bound to the support, to form a π-complex between the supported transition metal and the unsaturated organic substrate molecule; wherein the transition metal is attached to the solid support by a linking ligand that is a phosphine, phosphite or isonitrile, and the transition metal is cobalt or chromium.

5. A method of performing chemical modification to an unsaturated organic molecule which method comprises:

(A) attaching to a solid support via a transition metal complex traceless linker the unsaturated organic molecule;

(B) performing at least one chemical modification to the unsaturated organic molecule;

(C) releasing the unsaturated organic molecule from the transition metal complex traceless linker;

wherein the transition metal is attached to the solid support by a linking ligand that is a phosphine, phosphite or isonitrile, and the transition metal is cobalt or chromium.

6. A method as claimed in claim 5 wherein the chemical modification is a chemical synthesis being either by combinatorial chemistry or by multiple parallel synthesis.

7. A method of tagging a support within a chemical synthesis comprising for each reaction step desired to be labelled contacting a transition metal complex containing an exchangeable ligand bound to the support with a tagging ligand unique for the reaction being performed; wherein the transition metal is attached to the solid support by a linking ligand that is a phosphine, phosphite or isonitrile, and the transition metal is cobalt or chromium.

8. A method of tagging a support within a chemical synthesis comprising for each reaction step desired to be labelled contacting a transition metal complex with a reactive group capable of making an analyzable modification on one of the ligands of the transition metal complex unique for the reaction being performed; wherein the transition metal is attached to the solid support by a linking ligand that is a phosphine, phosphite or isonitrile, and the transition metal is cobalt or chromium.

* * * * *

UNITED STATES PATENT AND TRADEMARK OFFICE
CERTIFICATE OF CORRECTION

PATENT NO.   : 6,821,783 B1  
DATED        : November 23, 2004  
INVENTOR(S)  : Alex Comely et al.

It is certified that error appears in the above-identified patent and that said Letters Patent is hereby corrected as shown below:

Column 12,
Line 67, replace "η" with -- π --.

Signed and Sealed this

Twenty-ninth Day of November, 2005

JON W. DUDAS
*Director of the United States Patent and Trademark Office*